United States Patent
John et al.

[11] Patent Number: 6,111,125
[45] Date of Patent: Aug. 29, 2000

[54] PREPARATION OF (1R,4S)-4-HYDROXY-1,2,2-TRIMETHYLCYCLOPENTYL METHYL KETONE AND DERIVATIVES AND STEREOISOMERS OF THIS COMPOUND

[75] Inventors: Michael John, Ludwigshafen; Udo Rheude, Otterstadt; Joachim Paust, Neuhofen; Joachim Meyer, Maxdorf, all of Germany

[73] Assignee: BASF Aktiengesellschaft, Ludwigshafen, Germany

[21] Appl. No.: 08/398,643

[22] Filed: Mar. 3, 1995

[30] Foreign Application Priority Data

Mar. 7, 1994 [DE] Germany ............... 44 07 464

[51] Int. Cl.$^7$ ........................................... C07F 7/08
[52] U.S. Cl. ............... 556/436; 556/437; 556/482; 549/215; 549/546; 568/361; 568/377; 568/667; 568/823; 568/825
[58] Field of Search ................. 549/546, 215; 556/437, 482, 436; 568/361, 377, 667, 823, 825

[56] References Cited

U.S. PATENT DOCUMENTS

| | | | |
|---|---|---|---|
| 5,155,243 | 10/1992 | Fujiwa et al. | 549/546 |
| 5,382,676 | 1/1995 | Kuwana et al. | 549/541 |
| 5,424,460 | 6/1995 | Duhamel et al. | 549/546 |
| 5,565,489 | 10/1996 | Kaneko et al. | 514/475 |
| 5,801,123 | 9/1998 | Sakai et al. | 504/291 |

OTHER PUBLICATIONS

J. Chem. Soc. 1961, 00 4019 f.
Helv. Chim. Acta 66, 7 (1983) No. 192, pp 1939–60
J. Mol Struct. 226 (1992) pp 91–92.
Quim Nova 14 (1991) pp 22–25.
Carrotinoid Chem. Biochem. Proc. Int. Symp. Carotenoids, 6th Meeting, Date 1981, pp. 71–86, edited by Britten G. Goodween T.W., Pergamon, Oxford.

Primary Examiner—Paul F. Shaver
Attorney, Agent, or Firm—Keil & Weinkauf

[57] ABSTRACT

A process for preparing 4-hydroxy-1,2,2-trimethylcyclopentyl methyl ketones of the general formula I, in particular of the (1R,4S)-4-hydroxy-1,2,2-trimethylcyclopentyl methyl ketone of the formula Ia

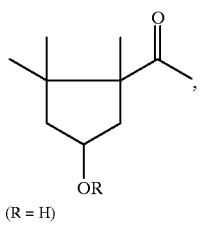

(I)

(R = H)

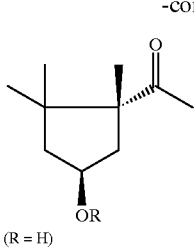

(Ia)

(R = H)

which is required for preparing the red dye capsorubin which is in demand, starts from 2,2,6-trimethylcyclohexanones of the general formula II

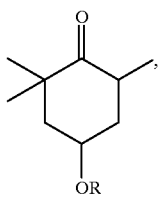

(II)

where R is hydrogen or a protective group, via the novel intermediates of the general formulae V and VI

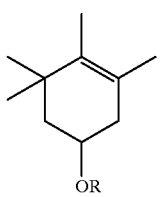

(V)

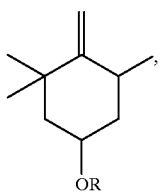

(VI)

by diastereoselective epoxidation and reaction of the resulting 7-oxabicyclo[4.1.0]heptanes of the general formula VIII

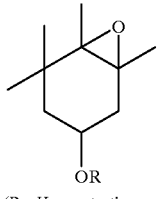

(VIII)

(R = H or protective group)

with Lewis acids and, where appropriate, removal of the protective group. Also claimed are the novel intermediates of the formula V and their (1S) and (1R) isomers and those of the formula VIII as well as their (1R,3S,6S), (1S,3S,6R) and (1R,3R,6S) isomers.

11 Claims, No Drawings

PREPARATION OF (1R,4S)-4-HYDROXY-1,2,2-TRIMETHYLCYCLOPENTYL METHYL KETONE AND DERIVATIVES AND STEREOISOMERS OF THIS COMPOUND

The invention relates to a process for the preparation of (1R,4S)-4-hydroxy-1,2,2-trimethylcyclopentyl methyl ketone and O-protected derivatives as essential precursors for the red dye capsorubin, which is in demand, and of stereoisomers of this compound, and to novel precursors of the general formulae V and VIII.

Capsorubin is, like capsanthin and cryptocapsin, a pigment of red paprika (*Capsicum annuum*) and has the following structure:

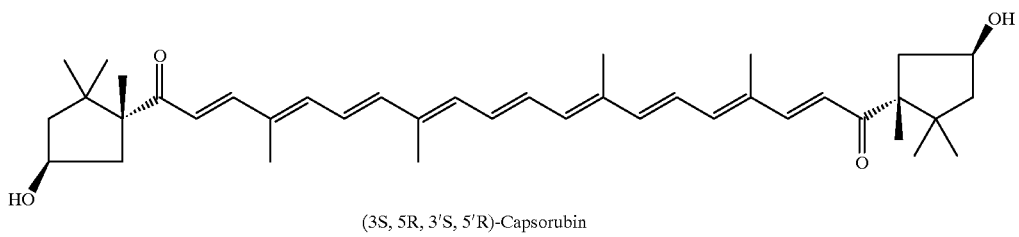

(3S, 5R, 3′S, 5′R)-Capsorubin

It is thus characteristic of this red pigment that cyclopentanol units are present in the molecule. The complicated stereochemistry of the capsorubin end groups is unusual for carotenoids and was not definitively elucidated until the 1960s (cf. J. Chem. Soc. 1961 4019 ff.).

The good coloring effect of capsorubin meant that early attempts were made to prepare it by synthesis. The first synthesis of optically inactive capsorubin was achieved by Weedon (cf. Pure Appl. Chem. 14 (1967) 265–78) in a sequence of 8 reaction stages, the last step being an aldol condensation of 2 equivalents of racemic 4-hydroxy-1,2,2-trimethylcyclopentyl methyl ketone with one equivalent of the $C_{20}$-dialdehyde crocetindialdehyde.

Once the synthesis of an appropriate cyclopentylcarboxylic ester with a center of chirality had succeeded in 4 stages starting from (+)-camphor (cf. Acta Chem. Scand. B 28 (1974) 492–500), as well as the preparation of the optically active end group of capsorubin from (3R)-3-hydroxy-β-cyclocitral (cf. Pure Appl. Chem. 51 (1979) 535–64), the way was free for synthesizing optically active capsorubin (cf. Helv. Chim. Acta 66 (1983) 1939–60).

Another successful route to optically active capsorubin started from (+)-camphor (cf. J. Mol. Struct. 226 (1992) 91–96) or isophorone (cf. Quim. Nova 14 (1991) 22–25) as source of the optically active cyclopentyl unit and crocetindialdehyde. The disadvantage of all the capsorubin syntheses described to date is that the individual reaction steps are too elaborate and thus unsuitable for industrial implementation.

However, since the aldol condensation, disclosed in Helv. Chim. Acta 66 (1983) 1939–60, of (1R,4S)-4-hydroxy-1,2,2-trimethylcyclopentyl methyl ketone with crocetindialdehyde can also be carried out quite well on the industrial scale, it was important for synthesizing capsorubin to develop a straightforward way of preparing (1R,4S)-4-hydroxy-1,2,2-trimethylcyclopentyl methyl ketone of the formula I or its O-protected derivatives.

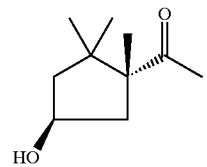

(I)

It is an object of the present invention to develop a way of preparing (1R,4S)-4-hydroxy-1,2,2-trimethylcyclopentyl methyl ketone and derivatives starting from an easily obtainable starting material in the minimum number of reaction steps which can easily be carried out industrially.

We have found that this object is achieved by a process for preparing 1,2,2-trimethylcyclopentyl methyl ketone derivatives of the general formula I

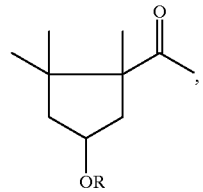

(I)

where R is hydrogen or alkyl, aryl, arylmethyl, trialkylsilyl, triarylsilyl, alkylarylsilyl, alkoxyalkyl, tetrahydropyranyl, arylmethyloxycarbonyl, alkanoyl or benzoyl, preferably hydrogen or tert-butyl, isopropyl, benzyl, alkylbenzyl, 2-napthylmethyl, tert-butyldimethylsilyl, benzyloxycarbonyl, tetrahydropyranyl, ethoxyethyl, acetyl, benzoyl or methoxyisopropyl which comprises A. reacting a 2,2,6-trimethyl-1-cyclohexanone of the general formula II

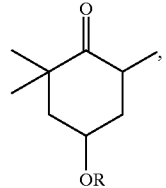

(II)

where R is hydrogen or one of the abovementioned radicals, with a methyl carbanion of the general formula III

$CH_3$—M⁺        (III), where M is Li, MgCl, MgBr or MgI, and converting the resulting 1,4-dihydroxy-1,2,2,6-tetramethylcyclohexane derivative of the general formula IV

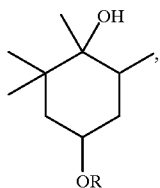

(IV)

where R is hydrogen or one of the abovementioned radicals, acid-catalyzed elimination of the tertiary hydroxyl group into a mixture of compounds of the formulae V and VI

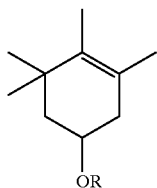

(V)

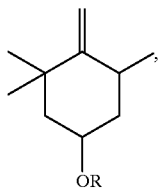

(VI)

or else converting the 2,2,6-trimethyl-1-cyclohexanone of the general formula II in a Wittig reaction with a methylenetri-phenylphosphorane of the formula VII

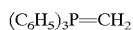

$(C_6H_5)_3P=CH_2$ (VII)

directly into the compound of the general formula VI,
B. converting the resulting compound of the general formula VI by acid-catalyzed double-bond isomerization into the compound of the general formula V,
C. epoxidizing the double bond in the compound of the general formula V

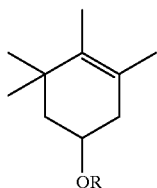

(V)

where R has the abovementioned meaning by reaction with peroxy acids, their salts or hydroperoxides in a conventional way, and
D. converting the resulting 7-oxabicyclo[4.1.0]heptane derivatives of the general formula VIII

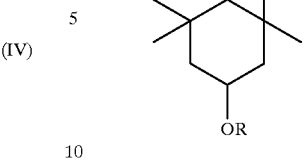

(VIII)

by reaction with Lewis acids and, where appropriate, elimination of the protective group on the oxygen in a conventional way into the 1,2,2-trimethylcyclopentyl methyl ketones of the general formula I.

Although it was disclosed in Carotenoid Chem. Biochem. Proc. Int. Symp. Carotenoids, 6th Meeting, Date 1981, pages 71–86, especially 78–79, Edited by: Britton G,; Goodwen T. W., Pergamon, Oxford, that it is possible by epoxidation of optically active 1-acetoxy-3,4,5,5-tetramethyl-3-cyclohexene derivatives to prepare optically active 3-acetoxy-7-oxa-1,5,5,6-tetramethylbicyclo[4.1.0]heptanes and convert the latter by reaction with Lewis acids into optically active 4-hydroxy-1,2,2-trimethylcyclopentyl methyl ketones, on the one hand the preparation described herein of the starting compound from hydroxycyclocitral is industrially very elaborate, and on the other hand sufficient stereocontrol of the reaction cannot be attained by the acetoxy group used as protective group in this case.

To prepare the (1R,4S)-4-hydroxy-1,2,2-trimethylcyclopentyl methyl ketone of the general formula Ia

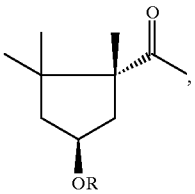

(Ia)

where R is hydrogen, which is in particular demand as capsorubin precursor, the procedure in the process according to the invention is such that in step C. a (1S)-3,4,5,5-tetramethyl-3-cyclohexene derivative of the general formula Va

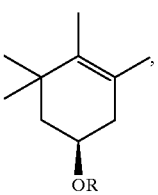

(Va)

where R is tert-butyl, isopropyl, benzyl, alkylbenzyl, 2-naphthylmethyl or tert-butyldimethylsilyl, is stereoselectively epoxidized, and in step D. the resulting (1R,3S,6S)-7-oxabicyclo[4.1.0]heptane derivative of the general formula VIIIa

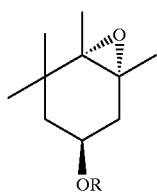

(VIIIa)

is reacted with a Lewis acid, and subsequently the protective group is eliminated in a conventional way.

The advantageous procedure according to the invention for preparing (1R,4S)-4-hydroxy-1,2,2-trimethylcyclopentyl methyl ketone, which is provided with a protective group where appropriate, of the general formula Ia

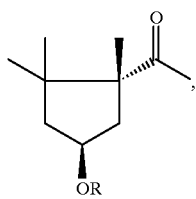

(Ia)

where R is hydrogen, tert-butyl, isopropyl, benzyl, alkylbenzyl, 2-naphthylmethyl or tert-butyldimethylsilyl, in step A. a (4R,6R)-4-hydroxy-2,2,6-trimethyl-1-cyclohexanone of the general formula IIa

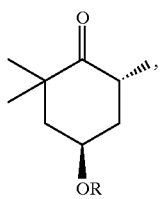

(IIa)

where R is hydrogen, is used and is converted as described above in steps A. and B. onto the (1S)-3,4,5,5-tetramethyl-3-cyclohexen-1-ol of the general formula Va

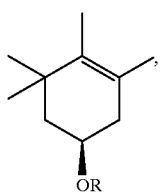

(Va)

where R is hydrogen, and subsequently the hydroxyl group in Va is provided in a conventional way with a bulky, non-coordinating and complexing protective group, C. the resulting (1S)-3,4,5,5-tetramethyl-3-cyclohexen-1-ol derivative of the general formula Va

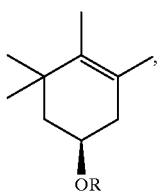

(Va)

where R is preferably tert-butyl, isopropyl, benzyl, alkylbenzyl, 2-naphthylmethyl or tert-butyldimethylsilyl, is stereoselectively epoxidized and D. the resulting (1R,3S,6S)-7-oxabicyclo[4.1.0]heptane derivative of the general formula VIIIa

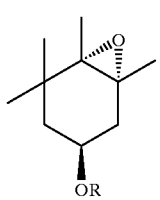

(VIIIa)

where R has the meanings stated under C. for compound Va, is reacted with a Lewis acid and, if required, the protective group is removed in a conventional way.

The general procedure according to the invention for preparing a (1S,4S)-1,2,2-trimethylcyclopentyl methyl ketone of the general formula Ib

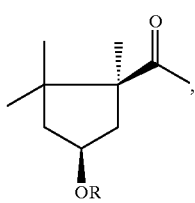

(Ib)

where R is hydrogen or benzyloxycarbonyl, tetrahydropyranyl, ethoxyethyl, acetyl or methoxyisopropyl, is in step C to epoxidize diastereoselectively a (1S)-3,4,5,5-tetramethyl-3-cyclohexen-1-ol derivative of the general formula Va

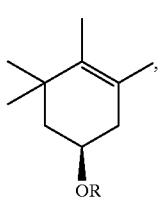

(Va)

where R is hydrogen or one of the radicals mentioned above for the ketone Ib,

D. to react the resulting (1S,3S,6R)-7-oxa-1,5,5,6-tetramethylbicyclo[4.1.0]heptane of the general formula VIIIb

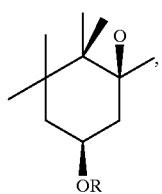

(VIIIb)

with a Lewis acid and, if required, to remove the protective group in a conventional way.

The advantageous procedure according to the invention for preparing a (1S,4S)-1,2,2-trimethylcyclopentyl methyl ketone of the general formula Ib

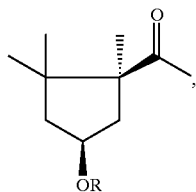

(Ib)

where R is hydrogen, is to use a (4R,6R)-2,2,6-trimethyl-1-cyclohexanone derivative of the general formula IIb

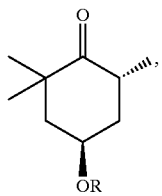

(IIb)

where R is H or benzyloxycarbonyl, tetrahydropyranyl, ethoxyethyl, acetyl or methoxyisopropyl, to convert the latter by steps A. and B. described above into a (1S)-3,4-,5,5- tetramethyl-3-cyclohexene derivative of the general formula Va

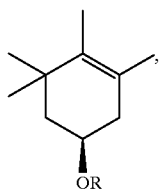

(Va)

where R is hydrogen or one of the radicals mentioned above for the cyclohexanone IIb, C. to epoxidize the latter stereoselectively and D. to react the resulting (1S,3S,6R)-7-oxa-1,5,5,6-tetramethyl-bicyclo[4.1.0]heptane derivative of the general formula VIIIb

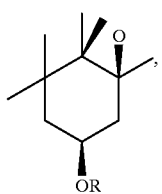

(VIIIb)

with a Lewis acid and to remove the protective group in a conventional way.

of the intermediates in this advantageous process of the invention, the 1,4-dihydroxy-1,2,2,6-tetramethylcyclohexane derivatives of the general formula IV

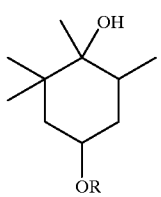

IV (R = protective group)

and their (1S) and (1R) isomers;

the 3,4,5,5-tetramethyl-3-cyclohexene derivatives of the general formula V

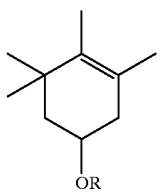

V (R = protective group)

and their (1S) and (1R) isomers;

the 3,5,5-trimethyl-4-methylenecyclohexane derivatives of the general formula VI

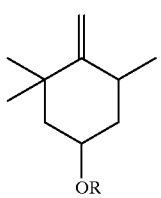

VI (R = protective group)

and their (1S) and (1R) isomers;

and the 7-oxa-1,5,5,6-tetramethylbicyclo[4.1.0]heptane derivatives of the general formula VIII

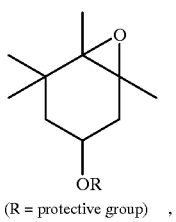

(VIII)

(R = protective group), and their (1R,3S,6S), (1R,3R,6S) and (1S,3S,6R) isomers are novel and are claimed as far as possible.

The 4-hydroxy-2,2,6-trimethyl-1-cyclohexanones of the general formula II

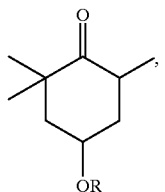

(II)

where R is hydrogen, which are required as starting materials for the process according to the invention can be obtained starting from oxoisophorone, which is easily obtainable industrially, by fermentative reduction and subsequent chemical reduction of the resulting optically active saturated ketone, and with suitable choice of the conditions there is formation predominantly of the (4R,6R) isomer which is required for the capsorubin synthesis (cf. Helv. Chim. Acta 59 (1976) 1832–49, especially 1839).

The introduction of protective groups on the hydroxyl group of the cyclohexanone can take place in a conventional way.

The methyl carbanions advantageously used to convert the 2,2,6-trimethyl-1-cyclohexanone derivatives of the general formula II into the 1,4-dihydroxycyclohexane derivatives of the general formula IV are methyl Grignard compounds such as $CH_3MgCl$, $CH_3MgBr$ and $CH_3MgI$, or else methyllithium. For further details of the procedure for the Grignard reaction and the reaction with methyllithium, reference may be made, for example, to "Organikum, Organisch-chemisches Grundpraktikum", 16th Edition, VEB Deutscher Verlag der Wissenschaften, Berlin 1986, pages 499–502. The reaction is generally carried out under a protective gas such as $N_2$.

Particularly suitable conditions for the acid-catalyzed elimination of the tertiary hydroxyl group from the 1,4-dihydroxy-1,2,2,6-tetramethylcyclohexane of the general formula IV are as follows: the 1,4-dihydroxycyclohexane derivatives of the general formula IV are briefly refluxed in an inert organic solvent which forms an azeotrope with water, with the addition of traces of an acid such as $H_2SO_4$, $H_3PO_4$ or p-toluenesulfonic acid, which results in selective elimination of the tertiary and not of the secondary hydroxyl. Under these conditions there is the simultaneous possibility of quantitative isomerization of the exo-methylene group in compounds of the general formula VI to the internal double bond of compounds of the general formula V.

The reaction of the 2,2,6-trimethyl-1-cyclohexanone derivatives of the general formula II with methylenetriphenylphosphoranes of the formula VII to give the methylenecyclohexane compounds of the general formula VI also takes place in a conventional way. For details of the procedure for Wittig reactions with cyclic ketones, reference may be made, for example, to "Organikum, Organisch-chemisches Grundpraktikum", 16th Edition, VEB Deutscher Verlag der Wissenschaften, Berlin 1986, pages 465–66.

The acid-catalyzed double-bond isomerization of the methylenecyclohexane compounds of the general formula VI to tetramethyl-1-cyclohexene derivatives of the general formula V

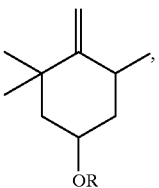

(VI)

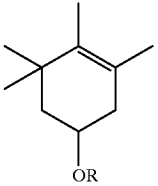

(V)

is generally carried out in inert organic solvents such as aliphatic or aromatic hydrocarbons or halogenated hydrocarbons, with the addition of catalytic amounts of an acid such as $H_2SO_4$, $H_3PO_4$ or p-toluenesulfonic acid, at from 60 to 150° C., preferably 80 to 140° C., in particular 90–120° C.

The isomerization is carried out either on the mixture of the compounds of the formula V and VI obtained in the reaction with methyl carbanions and subsequent elimination of water, or else the methylenecyclohexane of the formula VI obtained in the reaction with methylenetriphenylphosphorane.

Particularly suitable conditions for the subsequent epoxidation of the double bond in the compounds of the general formula V are as follows:

The epoxidizing agents generally used are peroxy acids such as peroxyformic acid, peroxyacetic, acid, peroxybenzoic acid, peroxytrifluoroacetic acid, monoperoxyphthalic acid, pertungstic acid, permolybdic acid or 3-chloroperoxybenzoic acid, salts of peroxy acids such as magnesium peroxyphthalate or pervanadate, or hydroperoxides such as tert-butyl hydroperoxide/$VO(CH_3—CO—CH_2—CO—)_3$; tert-butyl hydroperoxide/$MnO_2$ or $VO(CH_3—CO—CH_2—CO—)_3/H_2O_2$. The epoxidizing agent is generally used in amounts of from 1 to 1.8, preferably 1 to 1.5, especially 1 to 1.2, mol per mol of the compound of the general formula V, Va or Vb.

Particularly suitable solvents for this epoxidation are aliphatic or aromatic hydrocarbons or halogenated hydrocarbons.

Suitable reaction temperatures are from −30 to +40° C., preferably −10 to +30° C., especially −5 to +25° C.

The epoxidation is advantageously carried out with exclusion of light.

The epoxidation of (1S)-3,4,5,5-tetramethyl-3-cyclohexen-1-ol of the formula Va

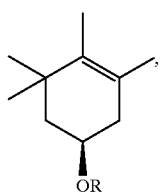
(Va)

where R is H, allows, utilizing the asymmetric induction, a diastereoselective synthesis of (1S,3S,6R)-7-oxa-1,5,5,6-tetramethylbicyclo[4.1.0]heptane of the general formula VIIIb

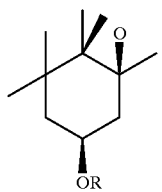
VIIIb where R is H.

The introduction of protective groups R with a strong donor function which lead to the formation of hydrogen bonds or serve for complexation of epoxidation catalysts makes it possible to increase the stereoselectivity for this type of reaction. Examples of protective groups with a strong donor function are: arylmethyloxycarbonyl groups such as benzyloxycarbonyl, alkyloxyalkyl groups such as ethoxyethyl and methoxyisopropyl, alkanoyl groups such as acetyl, arylalkanoyl groups such as benzoyl, or tetrahydropyranyl.

If, by contrast, a bulky protective group is introduced on the hydroxyl group of (1S)-3,4,5,5-tetramethyl-3-cyclohexen-1-ol of the formula Va, the diastereoselectivity of the epoxidation reaction is inverted.

Examples of bulky, non-coordinating and non-complexing protective groups are the following: bulky alkyl groups such as tert-butyl or isopropyl, aryl groups such as phenyl, an alkylphenyl, naphthyl or alkylnaphthyl group, or else arylmethyl groups such as benzyl or 2-naphthylmethyl, an alkylarylmethyl group such as tert-butylbenzyl, a trialkylsilyl group such as tert-butyldimethylsilyl, a triarylsilyl group such as triphenylsilyl or an alkylarylsilyl group such as dimethylphenylsilyl.

Reaction of the epoxides with such different stereochemistries with Lewis acids leads in a short time to a ring contraction to form the corresponding cyclopentyl methyl ketones. These ring contractions take place with high stereoselectivity. Whereas ring contraction of the epoxide with the syn orientation of the hydroxyl group leads to (1S,4S)-1,2,2-trimethylcyclopentyl methyl ketones of the formula Ib, ring contraction of the epoxide with the anti orientation of the hydroxyl group provides the (1R,4S)-4-hydroxy-1,2,2-trimethylcyclopentyl methyl ketone, or its derivatives of the formula Ia, required to prepare the capsorubin.

By contrast, if the starting compound used for the process according to the invention is a (4S,6R)-4-hydroxy-2,2,6-trimethyl-1-cyclohexanone derivative of the general formula IIc

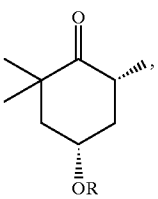
(IIc)

where R is hydrogen or benzyloxycarbonyl, tetrahydropyranyl, ethoxyethyl, acetyl, benzoyl, alkylbenzoyl or methoxyisopropenyl, steps A. and B. according to the invention result in a (1R)-3,4,5,5-tetramethyl-3-cyclohexene of the general formula Vc which, on stereoselective epoxidation, gives a (1R,3R,6S)-7-oxa-1,5,5,6-tetramethylbicyclo[4.1.0]heptane derivative of the general formula VIIIc from which it is possible to prepare by reaction with Lewis acids, with ring contraction and elimination of the protective groups, a (1R,4R)-1,2,2-trimethylcyclopentyl methyl ketone of the formula Ic.

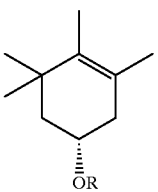
Vc

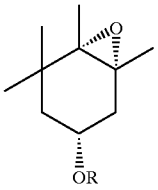
VIIIc

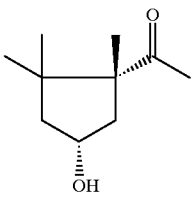
Ic

It is likewise possible to convert [1R,4R]-4-hydroxy-1,2,2-trimethylcyclopentyl methyl ketone into [1R,4S]-4-hydroxy-1,2,2-trimethylcyclopentyl methyl ketone after previous ketalization by oxidation, enantioselective reduction and final ketal cleavage.

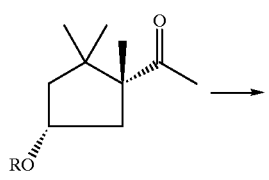

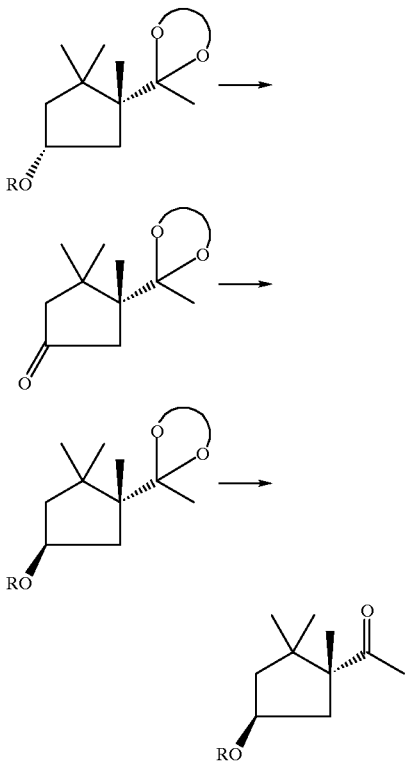

This sequence is less important for the preparation of capsorubin, however, because the number of stages is distinctly higher.

Examples of Lewis acids which can be used according to the invention are: $MgCl_2$, $MgBr_2$, $MgI_2$, $CaCl_2$, $CaBr_2$, $FeCl_3$, $AlCl_3$, $TiCl_4$, $SnCl_4$, $BF_3(C_2H_5)_2O$, $SbCl_3$ or $ZnCl_2$.

Those advantageously used are $FeCl_3$, $AlCl_3$, $TiCl_4$; $BF_3 \cdot (C_2H_5)_2O$ or $SnCl_4$, especially $FeCl_3$, $BF_3(C_2H_5)_2O$ or $AlCl_3$. The Lewis acids are used in amounts of about 0.01 to 1 equivalent per equivalent of the epoxy compound.

It was very surprising that the ring contraction of the epoxides of the general formula VIIIa–c takes place virtually stereoselectively and, furthermore, the ring contraction gives essentially only one product, namely cyclopentyl methyl ketones of the general formulae I or Ia, Ib and Ic.

The process according to the invention can be used to prepare the (1R,4S)-4-hydroxy-1,2,2-trimethylcyclopentyl methyl ketone of the formula Ia with R=H, which is required for the industrial preparation of capsorubin, as well as derivatives or stereoisomers of this compound, using a starting material which is easily obtainable industrially, in a manner which is relatively simple industrially and gives good yields via novel intermediates.

EXAMPLE 1

Synthesis of (1S,4S)-4-hydroxy-1,2,2-trimethyl-cyclopentyl methyl ketone (Ib)

A. Preparation of (4R)-1,4-dihydroxy-1,2,2,6-tetramethylcyclohexane

A solution of 1.11 g (7.2 mmol) of (4R,6R)-4-hydroxy-2,6,6-trimethyl-1-cyclohexanone in 50 ml of absolute tetrahydrofuran (THF) was added dropwise to 9 ml of a 3 M solution of methylmagnesium bromide (26.6 mmol) in diethyl ether (ether) while maintaining room temperature (RT) by external cooling, under nitrogen as protective gas, over the course of minutes (min). This resulted in a cloudy yellowish solution which was then stirred at RT under $N_2$ for 12 hours (h). Subsequently, 10 ml of 5% by weight aqueous sulfuric acid were added to the mixture, which was then extracted twice with 50 ml of ether. Removal of the solvent by distillation resulted in 1.05 g of a crude product comprising a mixture of diastereomers in respect both of center 1 and of center 6.

B. Preparation of (1S)-3,4,5,5-tetramethyl-3-cyclohexen-1-ol 4 g (23.2 mmol) of a mixture of diastereomers obtained in Example 1A were taken up in 50 ml of toluene, a spatula-tip (about 4 mg) of p-toluenesulfonic acid (p-TsOH) was added to the solution, and the mixture was refluxed for 45 min. It was subsequently poured into 50 ml of water and extracted twice with 50 ml of ether. The resulting organic phase was washed with 50 ml of saturated aqueous $NaHCO_3$ solution, dried over $MgSO_4$ and freed of solvent under reduced pressure. The resulting crude product was chromatographed on 150 g of silica gel with a hexane/ethyl acetate (EA) mixture in the ratio 4:1. The desired product was obtained in the form of 2.5 g of pale yellow crystals with a purity of 96.4% (GC analysis). This corresponds to a selectivity of 71% of theory.

C. Preparation of (1S,3S,6R)-3-hydroxy-7-oxa-1,5,5,6-tetramethylbicyclo-[4.1.0]heptane 2.5 g (16.2 mmol) of the (1S)-3,4,5,5-tetramethyl-3-cyclohexen-1-ol obtained in Example 1B were dissolved in 50 ml of methylene chloride under $N_2$, the solution was cooled to 0° C., and then, with exclusion of light, 5.1 g of a 55% by weight solution of 3-chloroperoxybenzoic acid in methylene chloride (MCPBA; equivalent to 16.2 mmol) were added, and the mixture was stirred at RT for 1 h. The mixture was then poured into 50 ml of ice-water, and 50 ml of methylene chloride were added. After vigorous mixing, the organic phase was separated off, washed with 100 ml of water and then with 50 ml of 5% strength $Na_2CO_3$ solution and then with 50 ml of water and subsequently dried, and the solvent was removed to result in 2.56 g (corresponding to 93% of theory) of the desired epoxide. Chromatography on 75 g of silica gel with hexane/EA (4:1) resulted in 2.05 g of the desired compound. The yield of pure product was 75%, and the relative configuration was elucidated by 2D NMR experiments.

D. Preparation of (1S,4S)-4-hydroxy-1,2,2-trimethylcyclopentyl methyl ketone 1 g (5.87 mmol) of the (1S,3S,6R)-3-hydroxy-7-oxa-1,5,5,6-tetramethylbicyclo[4.1.0]heptane obtained in Example 1C. was dissolved in 25 ml of absolute (filtered through Alox B) methylene chloride and, at RT, 0.36 ml (5.88 mmol) of $BF_3 \cdot (C_2H_5)_2O$ was added twice to the solution, and the mixture was then stirred at RT for 2 h. The mixture was subsequently diluted with 25 ml of methylene chloride, washed with 25 ml of water and then dried. Removal of the solvent under reduced pressure resulted in 0.92 g of a reddish brown crude product. Chromatography on 50 g of silica gel with hexane/EA (5:1) yielded 321 mg of the abovementioned cyclopentyl methyl ketone. Comparison of the spectra of the isolated compound with literature data showed very good agreement. The relative configuration of the new stereocenter in the system was determined by CH correlation and ROESY spectroscopy (NMR methods of unambiguous assignment of H resonances and their spatial relationships).

EXAMPLE 2

Synthesis of (1R,4S)-4-hydroxy-1,2,2-trimethylcyclopentyl methyl ketone (Ia)

A. Preparation of (1R)-3,3,5-trimethyl-4-methylenecyclohexan-1-ol 0.79 g (6.86 mmol) of potassium tert-butoxide (KOtBu) was added to a solution of 2.5 g (6.86 mmol) of methyltriphenylphosphonium bromide in 10 ml of dimethyl sulfoxide (DMSO) under $N_2$, and the mixture was then stirred at RT for 30 min. 0.36 g (2.29 mmol) of (4R,6R)-4-hydroxy-2,2,6-trimethyl-1-cyclohexanone was added to this mixture, which was then stirred at RT for 5 min. during which a white precipitate appeared. The mixture was then stirred at 60° C. for 15 min, cooled to RT, poured into 150 ml of ice-water and extracted twice with 50 ml of methylene chloride. The organic phase was separated off, washed with 50 ml of a 5% strength aqueous $Na_2CO_3$ solution and 50 ml of water and dried over $MgSO_4$, and the solvent was removed under reduced pressure.

B. Preparation of (1S)-3,4,5,5-tetramethyl-3-cyclohexen-1-ol 4 g of (1R)-3,3,5-trimethyl-4-methylene-1-cyclohexanol obtained in Example 2A were dissolved in 50 ml of toluene, about 6 mg of p-toluenesulfonic acid were added and the mixture was refluxed for 45 min. It was then poured into 50 ml of water and extracted twice with 50 ml of ether. The organic phase was separated off, washed with 50 ml of saturated $NaHCO_3$ solution, dried over $MgSO_4$ and freed of solvent under reduced pressure. The residue was chromatographed on 150 g of silica gel with hexane/EA (4:1) to result in 3.7 g of the abovementioned product in the form of pale yellow crystals with a purity of 97% according to GC.

C. Preparation of (1S)-1-tert-butyldimethylsilyloxy-3,4,5,5-tetramethyl-3-cyclohexene 0.8 g (5.2 mmol) of the (1S)-3,4,5,5-tetramethyl-3-cyclohexen-1-ol obtained in Example 2B was dissolved in 5 ml of absolute methylene chloride, 0.5 ml of pyridine was added to the solution, and the mixture was cooled to 0° C. Subsequently 1.54 g (5.7 mmol) of tert-butyldimethylsilyl trifluorome-thanesulfonate were added and the mixture was stirred at 0° C. for 15 min and then poured into 10 ml of water. After extraction with 10 ml of methylene chloride, the organic phase was washed with 10 ml of 0.1 M $H_2SO_4$, 10 ml of saturated $NaHCO_3$ solution and 10 ml of water, dried over $MgSO_4$ and concentrated to result in 1.3 g (92% of theory) of the abovementioned product.

D. Preparation of (1R, 3S, 6S)-3-(tert-butyldimethylsilyloxy)-7-oxa-1,5,5,6-tetramethylbicyclo[4.1.0]heptane 1.25 g (4.7 mmol) of the (1S)-1-tert-butyldimethylsilyloxy-3,4,5,5-tetramethyl-3-cyclohexene obtained in Example 1C were dissolved in 25 ml of absolute methylene chloride, the solution was cooled to 0° C. and then 1.5 g of 3-chloroperoxybenzoic acid in methylene chloride (equivalent to 4.7 mmol) were added, and the mixture was stirred at 0° C. for 1 h and then poured into 25 ml of ice-water. Subsequently 25 ml of methylene chloride were added and, after vigorous mixing, the organic phase was separated off, washed with 25 ml of a 5% strength $Na_2SO_3$ solution and 25 ml of water, dried and freed of solvent to result in 1.18 g (88% of theory) of colorless crystals. The diastereomeric excess according to NMR analysis is 20%.

E. Preparation of (1R,4S)-4-hydroxy-1,2,2-trimethylcyclopentyl methyl ketone 1.1 g (3.87 mmol) of the (1R,3S,6S)-3-(tert-butyldimethylsilyloxy)-7-oxa-1,5,5,6-tetramethylbicyclo[4.1.0]heptane obtained in Example 2D were dissolved in 25 ml of methylene chloride and, at RT, 0.24 ml (1.93 mmol) of $BF_3 \cdot (C_2H_5)_2O$ was added, the mixture was stirred at RT for 1 h, then 25 ml of water were added, and the organic phase was separated off, washed with water and concentrated. For quantitative removal of the protective group, 3.7 ml (6.1 mmol) of 1.1 M tetrabutylammonium fluoride solution were added to the residue. The mixture was again washed with water, and the organic phase was separated off. Chromatography on silica gel with a hexane/EA (5:1) mixture yielded 0.9 g of a product with a diastereomeric excess of 20%.

EXAMPLE 3

Synthesis of (1R,4S)-4-hydroxy-1,2,2-trimethylcyclopentyl methyl ketone (Ia)

A. Preparation of (1S)-1-benzyloxy-3,4,5,5-tetramethyl-3-cyclohexene 2 g (13 mmol) of (1S)-3,4,5,5-tetramethyl-3-cyclohexen-1-ol prepared in Examples 1A and 1B were dissolved in 10 ml of dimethoxyethane (DME) and, to form the alcoholate, added dropwise to a suspension of 965 mg (38.9 mmol) of NaH in 10 ml of DME at RT. After evolution of gas had ceased, 14 mmol of benzyl bromide were added dropwise. Reaction was complete after stirring at RT for 12 h. 50 ml of water were then added to the mixture, which was extracted twice with 50 ml of ether. Chromatography of the residue with hexane/EA (4:1) yielded 3 g (86%) of the abovementioned product.

B. Preparation of (1R,3S,6S)-3-benzyloxy-7-oxa-1,5,5,6-tetramethylbicyclo-[4.1.0]heptane 1.9 g (7.77 mmol) of the (1S)-1-benzyloxy-3,4,5,5-tetramethyl-3-cyclohexene prepared in Example 3A were dissolved in 40 ml of methylene chloride and cooled to 0° C. 2.44 g of 3-chloroperoxybenzoic acid in methylene chloride (equivalent to 7.77 mmol) were added, and the mixture was stirred at 0° C. for 1 h; it was subsequently poured into 150 ml of ice-water and extracted twice with 50 ml of methylene chloride. The organic phases were then washed with 50 ml of 5% strength sodium sulfite solution and 50 ml of water, dried and freed of solvent to result in 2 g (96%) of product. The diastereomeric excess is 65%.

C. Preparation of (1R,4S)-4-hydroxy-1,2,2-trimethylcyclopentyl methyl ketone 1.64 g (6.5 mmol) of the (1R,3S,6S)-3-benzyloxy-7-oxa-1,5,5,6-tetramethylbicyclo[4.1.0]heptane prepared in Example 3B were dissolved in 25 ml of methylene chloride and, at RT, 0.4 ml of boron trifluoride etherate was added. The mixture was stirred at RT for 1 h and then worked up as in Example 2E. Chromatography resulted in 0.98 g of product. To eliminate the protective group, the residue was taken up in 50 ml of ethanol, 150 mg of 10% Pd/C were added, and hydrogenation was carried out at RT under atmospheric pressure. The hydrogenation was complete after 45 min. The catalyst was removed and the solvent was removed under reduced pressure to result in 0.96 g of the abovementioned product with a diastereoselectivity of 65%.

EXAMPLE 4

Synthesis of (1R,4S)-4-hydroxy-1,2,2-trimethylcyclopentyl methyl ketone (Ia)

A. Preparation of (1S)-1-(2-naphthylmethyloxy)-3,4,5,5-tetramethyl-3-cyclohexene 2 g (13 mmol) of (1S)-3,4,5,5-tetramethyl-3-cyclohexen-1-ol prepared in Examples 2A and 2B were dissolved in 10 ml of DME and added dropwise to a suspension of 965 mg (38.9 mmol) of NaH in 10 ml of DME at RT. After evolution of gas had ceased, 14 mmol of 2-bromomethylnaphthalene were added dropwise. Reaction was complete after stirring at RT for 12 h. 50 ml of water were added to the mixture, which was then extracted twice with 50 ml of ether. Chromatography of the residue as in Example 3A resulted in 3.7 g (97%) of the abovementioned product.

B. Preparation of (1R,3S,6S)-3-(2-naphthylmethyloxy)-7-oxa-1,5,5,6-tetramethylbicyclo[4.1.0]heptane 4 g (13.6 mmol) of (1S)-1-(2-naphthylmethyloxy)-3,4,5,5-tetramethyl-3-cyclohexene prepared in Example 4A were reacted with 4.3 g (13.6 mmol) of 55% strength MCPBA as in Example 2D.

4.1 g of the abovementioned product were obtained (corresponding to 97% of theory) with a diastereoselectivity of 68%.

C. Preparation of (1R,4S)-4-hydroxy-1,2,2-trimethylcyclopentyl methyl ketone 4 g (1.3 mmol) of (1R,3S,6S)-3-(2-naphthylmethyloxy)-7-oxa-1,5,5,6-tetramethylbicyclo[4.1.0]heptane were reacted in methylene chloride with boron trifluoride etherate as in Example 3C. After the hydrogenation, the catalyst and solvent were removed to result in the abovementioned product with a diastereoselectivity of 78%. The diastereomers were separated by simple distillation.

EXAMPLE 5

Synthesis of (1R,4S)-4-hydroxy-1,2,2-trimethylcyclopentyl methyl ketone (Ia)

A. Preparation of (1S)-1-(4-tert-butylbenzyloxy)-3,4,5,5-tetramethyl-3-cyclohexene The abovementioned product was obtained in a 97% yield by reaction of (1S)-3,4,5,5-tetramethyl-3-cyclohexen-1-ol in DME with 4-tert-butylbenzyl bromide as in Example 3A.

B. Preparation of (1R,3S,6S)-3-(4-tert-butylbenzyloxy)-7-oxa-1,5,5,6-tetramethylbicyclo[4.1.0]heptane The abovementioned product was obtained in a yield of 92% by reaction of the (1S)-1-(4-tert-butylbenzyloxy)-3,4,5,5-tetramethyl-3-cyclohexene obtained in Example 5A with MCPBA as in Example 3B.

C. Preparation of (1R,4S)-4-hydroxy-1,2,2-trimethylcyclopentyl methyl ketone (Ia)

Ia was obtained with a diastereomeric excess of 78% by reacting the epoxide obtained in Example 5B with $BF_3$ etherate in methylene chloride as in Example 3C. The diastereomers can be separated by distillation or chromatography.

EXAMPLE 6

Preparation of (1S,4S)-4-hydroxy-1,2,2-trimethylcyclopentyl ethyl ketone (Ib)

A. Preparation of (1S)-1-ethoxyethoxy-3,4,5,5-tetramethyl-3-cyclohexene 0.8 g (5.2 mmol) of (1S)-3,4,5,5-tetramethyl-3-cyclohexen-1-ol was dissolved under $N_2$ in 5 ml of absolute methylene chloride, the solution was cooled to 0° C. and 260 mg (1.04 mmol) of pyridinium p-toluenesulfonate, and then 0.45 mg (6.2 mmol) of ethyl vinyl ether were added. The mixture was subsequently stirred at 0° C. for 1 h and then poured into a saturated aqueous $NaHCO_3$ solution, and the mixture was extracted with methylene chloride, and the extract was dried over $MgSO_4$ and concentrated. The residue was purified by distillation to yield 1.1 g (corresponding to 97% of theory) of the abovementioned product.

B. Preparation of (1R,3S,6S)-3-(ethoxyethoxy)-7-oxa-1,5,5,6-tetramethylbicyclo[4.1.0]heptane 0.6 g (2.65 mmol) of (1S)-1-ethoxyethoxy-3,4,5,5-tetramethyl-3-cyclohexene was dissolved in 12 ml of methylene chloride, the solution was cooled to 0° C., then 0.83 g of a 55% strength solution of 3-chloroperbenzoic acid in methylene chloride (equivalent to 2.65 mmol) was added, and the mixture was then stirred at 0° C. for 1 h. Workup as in Example 2D resulted in 0.9 g (82% of theory) with a diastereomeric excess of about 60%.

C. Preparation of (1S,4S)-4-hydroxy-1,2,2-trimethylcyclopentyl methyl ketone 1.2 g (4.95 mmol) of (1S,3S,6R)-3-(ethoxyethoxy)-7-oxa-1,5,5,6-tetramethylbicyclo-[4.1.0]heptane were dissolved in 25 ml of methylene chloride and, at RT, 0.3 ml (2.48 mmol) of boron trifluoride etherate was added. After stirring at RT for 1 h, the mixture was poured into 25 ml of water and extracted with 25 ml of methylene chloride. To eliminate the protective group, 2 ml of 0.1 M sulfuric acid were added to the organic phase and the mixture was stirred at RT for 1 h. The organic phase was subsequently washed several times with water, dried over magnesium sulfate and freed of solvent. Chromatography with hexane/EA (3:1) resulted in 0.39 g of product with a diastereomeric excess of 60%.

EXAMPLE 7

A. Preparation of (1S)-1-tetrahydropyranyloxy-3,4,5,5-tetramethyl-3-cyclohexene 0.8 g (5.2 mmol) of (1S)-3,4,5,5-tetramethyl-3-cyclohexen-1-ol prepared in Example 2A was dissolved in 5 ml of absolute methylene chloride under $N_2$, the solution was cooled to 0° C., and then firstly 260 mg (1.04 mmol) of pyridinium p-toluenesulfonate and then 450 mg (6.2 mmol) of 3,4-dihydropyran were added. The mixture was subsequently stirred at 0° C. for 1 h and then poured into saturated $NaHCO_3$ solution and extracted with methylene chloride. The extract was dried over $MgSO_4$ and concentrated to result in 1.1 g (corresponding to 89% of theory) of the desired product.

This compound can be converted into (1S,4S)-4-hydroxy-1,2,2-trimethylcyclopentyl methyl ketone as in Examples 6B and 6C.

EXAMPLE 8

Preparation of (1S)-1-benzyloxycarbonyl-3,4,5,5-tetramethyl-3-cyclohexene 2 g (13 mmol) of (1S)-3,4,5,5-tetramethyl-3-cyclohexen-1-ol were dissolved in 20 ml of abs. methylene chloride. At RT, 1 ml (13 mmol) of pyridine and 1.5 ml (13 mmol) of benzyl chloroformate were added. The mixture was stirred at RT for 4 h and then poured into 100 ml of ice-water. After extraction with methylene chloride, the organic phase was washed with 50 ml of 0.1 M sulfuric acid, 50 ml of saturated sodium bicarbonate solution and 50 ml of water. Drying and removal of the solvent resulted in 2.8 g (98%) of the abovementioned product.

This compound can be converted by epoxidation and treatment with $BF_3$ etherate as in Examples 6B and 6C. into (1S,4S)-4-hydroxy-1,2,2-trimethylcyclopentyl methyl ketone (Ib).

EXAMPLE 9

Preparation of (1R,4R)-4-hydroxy-1,2,2-trimethylcyclopentyl methyl ketone (Ic)

A Preparation of (4S)-1,4-dihydroxy-1,2,2,6-tetramethylcyclohexane

This compound can be obtained from (4S,6R)-4-hydroxy-2,6,6-trimethyl-1-cyclohexanone as in Example 1A.

B Preparation of (1R)-3,4,5,5-tetramethyl-3-cyclohexen-1-ol

This compound can be obtained from that of Example 9A as in Example 1B.

C Preparation of (1R,3R,6S)-3-hydroxy-7-oxa-1,5,5,6-tetramethyl-bicyclo[4.1.0]heptane Synthesis takes place as in Example 1C. and provides the abovementioned compound in comparable yield.

D Preparation of (1R,4R)-4-hydroxy-1,2,2-trimethylcyclopentyl methyl ketone

Reaction of (1R,3R,6S)-3-hydroxy-7-oxa-1,5,5,6-tetramethyl-bicyclo[4.1.0]heptane as in Example 1D led to the abovementioned compound in comparable yields and diastereo-selectivities.

We claim:

1. A process for preparing 1,2,2-trimethycyclopentyl methyl ketone derivatives of the general formula I

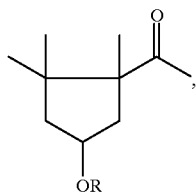

(I)

where R is hydrogen or alkyl, aryl, arylmethyl, trialkylsilyl, triarylsilyl, alkylarylsilyl, alkoxyalkyl, tetrahydropyranyl, arylmethyloxycarbonyl, alkanoyl or benzoyl, which comprises A. reacting a 2,2,6-trimethyl-1-cyclohexanone of the general formula II

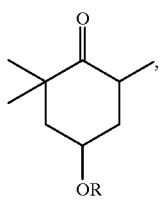

(II)

where R has the abovementioned meanings, with a methyl carbanion of the general formula III

 (III), where M⁺ is Li, MgCl, MgBr or MgI, and converting the resulting 1,4-dihydroxy-1,2,2,6-tetramethylcyclohexane derivative of the general formula IV

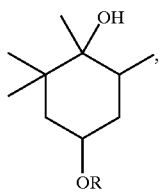

(IV)

where R has the abovementioned meanings, by acid-catalyzed elimination of the tertiary hydroxyl group into a mixture of compounds of the formulae V and VI

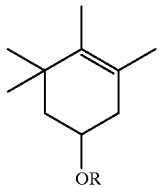

(V)

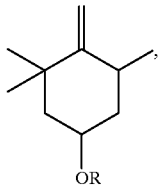

(VI)

where R has the abovementioned meanings, or else converting the 2,2,6-trimethyl-1-cyclohexanone of the general formula II in a Wittig reaction with a methylenetriphenylphosphorane of the formula VII

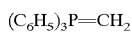 (VII)

directly into the compound of the general formula VI,

B. converting the resulting compound of the general formula VI by acid-catalyzed double-bond isomerization into the compound of the general formula V, C. epoxidizing the double bond in the compound of the general formula V

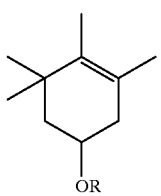

(V)

by reaction with peroxy acids, their salts or hydroperoxides in a conventional way, and D. converting the resulting 7-oxabicyclo[4.1.0]heptanes of the general formula VIII

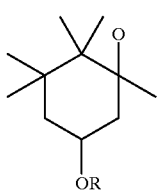

(VIII)

by reaction with Lewis acids and, where appropriate, elimination of the protective group on the oxygen into the 1,2,2-trimethylcyclopentyl methyl ketones of the general formula I.

2. A process as claimed in claim 1, wherein, for the preparation of (1R,4S)-1,2,2-trimethylcyclopentyl methyl ketone derivates of the general formula Ia

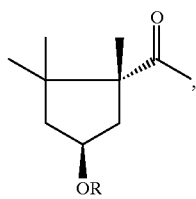

(Ia)

where R is hydrogen or tert-butyl, isopropyl, benzyl, alkylbenzyl, 2-naphthylmethyl, trialkylsilyl, triarylsilyl or alkylarylsilyl, in step C. a (1S)-3,4,5,5-tetramethyl-3-cyclohexene derivate of the general formula Va

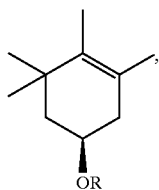

(Va)

where R is tert-butyl, isopropyl, benzyl, alkylbenzyl, 2-naphthylmethyl, trialkylsilyl, triarylsilyl or alkylarylsilyl, is epoxidized, and in step D. the resulting (1R,3S,6S)-7-oxa-bicyclo[4.1.0]heptane of the general formula VIIIa

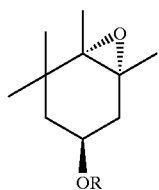

(VIIIa)

is reacted with a Lewis acid and, if required, the protective group is eliminated in a conventional way.

3. A process as claimed in claim 1, wherein, for the preparation of a (1R,4S)-4-hydroxy-1,2,2-trimethylcyclopentyl methyl ketone, which is provided with a protective group where appropriate, of the general formula Ia

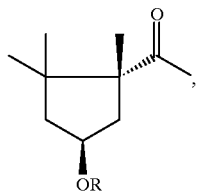

(Ia)

where R is hydrogen, tert-butyl, benzyl, alkylbenzyl, 2-naphthylmethyl or tert-butyldimethylsilyl, in step A. a (4R,6R)-2,2,6-trimethyl-1-cyclohexanone derivative of the general formula IIa

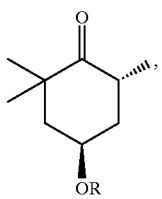

(IIa)

where R is hydrogen, is used and is converted as in steps A. and B. in claim 1 into the (1S)-3,4,5,5-tetramethyl-3-cyclohexen-1-ol of the general formula Va

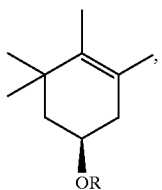

(Va)

where R is hydrogen, and subsequently the hydroxyl group is provided in a conventional way with one of the abovementioned bulky, non-coordinating and complexing protective groups, C. the resulting (1S)-3,4,5,5-tetramethyl-3-cyclohexen-1-ol derivative of the general formula Va

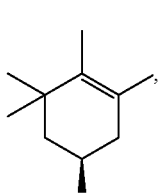

(Va)

where R is tert-butyl, isopropyl, benzyl, alkylbenzyl, 2-naphthylmethyl or tert-butyldimethylsilyl, is stereoselectively epoxidized and D. the resulting (1R,3S,6S)-7-oxabicyclo[4.1.0]heptane derivative of the general formula VIIIa

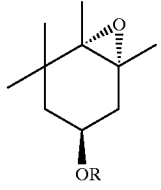

(VIIIa)

where R has the meanings stated under C. for compound Va, is reacted with a Lewis acid and, if required, the protective group is removed in a conventional way.

4. A process as claimed in claim 1, wherein, for the preparation of a (1S,4S)-1,2,2-trimethylcyclopentyl methyl ketone derivative of the general formula Ib (Ib)

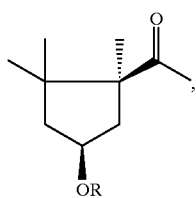

where R is hydrogen or benzyloxycarbonyl, tetrahydropyranyl, ethoxyethyl, acetyl or methoxyisopropyl, in step C. a (1S)-3,4,5,5-tetramethyl-3-cyclohexene derivative of the general formula Va (Va)

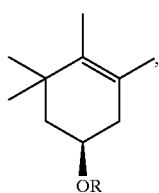

where R is hydrogen or one of the radicals mentioned for Ib, is diastereoselectively epoxidized, D. the resulting (1S,3S,6R)-7-oxa-1,5,5,6-tetramethylbicyclo[4.1.0]heptane derivative of the general formula VIIIb (VIIIb)

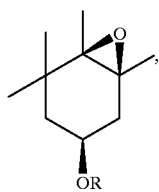

where R is hydrogen or one of the radicals mentioned above for Ib, is reacted with a Lewis acid and, if required, the protective group is removed in a conventional way.

5. A process as claimed in claim 1, wherein, for the preparation of a (1S,4S)-1,2,2-trimethylcyclopentyl methyl ketone of the general formula Ib (Ib)

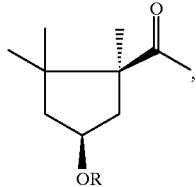

where R is hydrogen or benzyloxycarbonyl, tetrahydropyranyl, ethoxyethyl, acetyl or methoxyisopropyl, a (4R,6R)-2,2,6-trimethyl-1-cyclohexanone derivative of the general formula IIa (IIa)

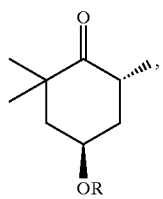

where R is H or a benzyloxycarbonyl, tetrahydropyranyl, ethoxyethyl, acetyl or methoxyisopropyl, is used and is converted as in steps A. and B. of claim 1 into a (1S)-3,4,5,5-tetramethyl-3-cyclohexene derivative of the general formula Va (Va)

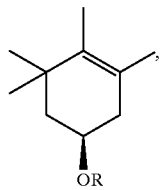

where R is hydrogen or benzyloxycarbonyl, tetrahydropyranyl, ethoxyethyl, acetyl or methoxyisopropyl, C. the latter is stereoselectively epoxidized and D. the resulting (1S,3S,6R)-7-oxa-1,5,5,6-tetramethylbicyclo[4.1.0]heptane derivative of the general formula VIIIb (VIIIb)

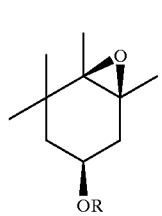

is reacted with a Lewis acid and, if required, the protective group is removed in a conventional way.

6. A process as claimed in claim 1, wherein, for the preparation of a (1R,4R)-1,2,2-trimethylcyclopentyl methyl ketone derivative of the formula Ic (Ic)

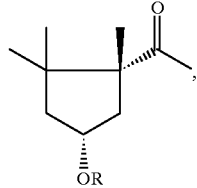

where R is hydrogen or benzyloxycarbonyl, tetrahydropyranyl, ethoxyethyl, acetyl or methoxyisopropyl, in step C. a (1R)-3,4,5,5-tetramethyl-3-cyclohexene derivative of the general formula Vb (Vb)

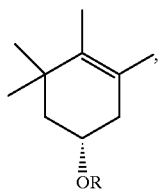

where R is hydrogen or one of the radicals mentioned above for Ic, is stereoselectively epoxidized and D. the resulting (1R,3R,6S)-7-oxa-1,5,5,6-tetramethylbicyclo[4.1.0]heptane derivative of the general formula VIIIc (VIIIc)

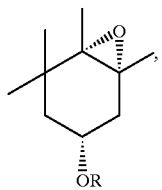

is reacted with a Lewis acid and, if required, the protective group is removed in a conventional way.

7. A process as claimed in claim 1, wherein, for the preparation of (1R,4R)-4-hydroxy-1,2,2-trimethylcyclopentyl methyl ketone of the general formula Ic (Ic)

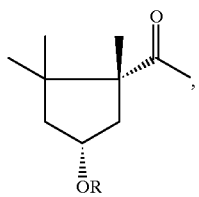

where R is H, in step C. a (1R)-3,4,5,5-tetramethyl-3-cyclohexene derivative of the general formula Vb (Vb)

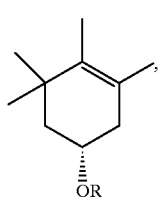

where R is hydrogen or benzyloxycarbonyl, tetrahydropyranyl, ethoxyethyl or methoxyisopropyl, is stereoselectively epoxidized, and in step D. the resulting (1R, 3R, 6S)-7-oxa-1,5,5,6-tetramethyl-bicyclo[4.1.0]heptane derivative of the general formula VIIIc (VIIIc)

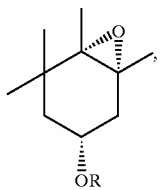

is reacted with a Lewis acid and, if required, the protective group is eliminated in a conventional way.

8. A 3,4,5,5-tetramethyl-3-cyclohexene derivative of the general formula V (V)

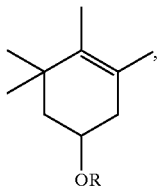

where R is hydrogen or tert-butyl, isopropyl, benzyl, alkylbenzyl, 2-naphthylmethyl, trialkylsilyl, triarylsilyl, alkylarylsilyl, benzyloxycarbonyl, tetrahydropyranyl, ethoxyethyl or methoxyisopropyl, and its (1S) and (1R) isomers of the formulae Va and Vb respectively (Va)

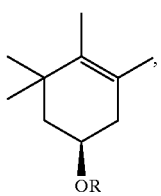

where R is tert-butyl, isopropyl, benzyl, alkylbenzyl, 2-naphthylmethyl, trialkylsilyl, triarylsilyl or alkylarylsilyl, (Vb)

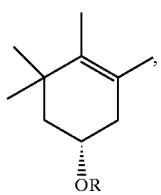

where R is benzyloxycarbonyl, tetrahydropyranyl, ethoxyethyl or methoxyisopropyl.

9. A 7-oxa-1,5,5,6-tetramethylbicyclo[4.1.0]heptane derivative of the general formula VIII

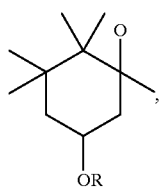

(VIII)

where R is tert-butyl, isopropyl, benzyl, alkylbenzyl, 2-naphthylmethyl, trialkylsilyl, triarylsilyl, alkylarylsilyl, benzyloxycarbonyl, tetrahydropyranyl, ethoxyethyl, acetyl or methoxyisopropyl, and its (1R, 3S,6S) isomer of the general formula VIIIa

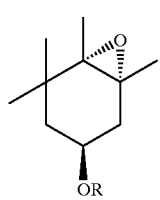

(VIIIa)

where R is tert-butyl, isopropyl, benzyl, alkylbenzyl, 2-naphthylmethyl or tert-butyldimethylsilyl; (1S,3S, 6R) isomer of the general formula VIIIb

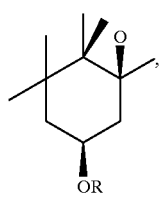

(VIIIb)

where R is benzyloxycarbonyl, tetrahydropyranyl, ethoxyethyl or methoxyisopropyl, and (1R,3R,6S) isomer of the general formula VIIIc

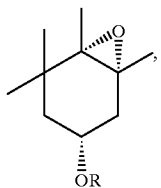

(VIIIc)

where R is benzyloxycarbonyl, tetrahydropyranyl, ethoxyethyl or methoxyisopropyl.

10. A (1S)-3,4,5,5-tetramethyl-3-cyclohexene derivative of the general formula Va

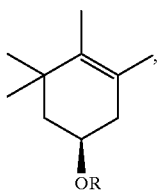

(Va)

where R is tert-butyl, isopropyl, benzyl, alkylbenzyl, 2-naphthylmethyl or tert-butyldimethylsilyl.

11. A (1R,3S,6S)-7-oxa-1,5,5,6-tetramethyl-bicyclo [4.1.0]heptane derivative of the general formula VIIIa

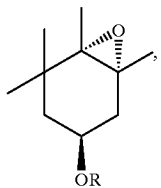

(VIIIa)

where R is tert-butyl, isopropyl, benzyl, alkylbenzyl, 2-naphthylmethyl or tert-butyldimethylsilyl.

* * * * *

UNITED STATES PATENT AND TRADEMARK OFFICE
CERTIFICATE OF CORRECTION

PATENT NO.: 6,111,125

DATED: August 29, 2000

INVENTOR(S): JOHN et al.

It is certified that error appears in the above-identified patent and that said Letters Patent is hereby corrected as shown below:

Col. 19, claim 1, line 1, "1,2,2-trimethycyclopentyl" should be
--1,2,2-trimethylcyclopentyl--.

Signed and Sealed this

Fifteenth Day of May, 2001

Attest:

NICHOLAS P. GODICI

Attesting Officer     Acting Director of the United States Patent and Trademark Office